United States Patent [19]

Nakabayashi et al.

[11] Patent Number: 5,637,610

[45] Date of Patent: Jun. 10, 1997

[54] COMPOSITION CONTAINING DIOXABICYCLO [3.3.0] OCTANE DERIVATIVE

[75] Inventors: Ayako Nakabayashi, Kyoto; Yoshinori Kitagawa; Kengo Akimoto, both of Ibaraki; Michihiro Sugano, Fukuoka, all of Japan

[73] Assignee: Suntory Limited, Osaka, Japan

[21] Appl. No.: 262,389

[22] Filed: Jun. 20, 1994

Related U.S. Application Data

[63] Continuation of Ser. No. 897,756, Jun. 12, 1992, abandoned.

[30] Foreign Application Priority Data

Jun. 15, 1991 [JP] Japan ................... 3-143715

[51] Int. Cl.$^6$ ................... A61K 31/355; A61K 31/34
[52] U.S. Cl. ................... 514/458; 514/469; 514/470; 514/824
[58] Field of Search ................... 514/458, 469, 514/470, 824

[56] References Cited

U.S. PATENT DOCUMENTS

| | | | |
|---|---|---|---|
| 4,427,694 | 1/1984 | Benecke et al. | 424/282 |
| 4,836,987 | 6/1989 | Shibata et al. | 422/101 |

FOREIGN PATENT DOCUMENTS

| | | |
|---|---|---|
| 0 207 735 | 6/1986 | European Pat. Off. . |
| 0 387 000 | 3/1990 | European Pat. Off. . |
| 0 409 654 | 7/1990 | European Pat. Off. . |
| 0 488 513 | 10/1991 | European Pat. Off. . |
| 60-224629 | 11/1985 | Japan . |
| 2-138120 | 5/1990 | Japan . |

OTHER PUBLICATIONS

Chemical Abstract No. 235163x (JP-A-62 172 086) (1992).
Yamashita et al., "Sesame Seed Lignans and γ-Tocopherol Act Synergistically to Produce Vitamin E Activity in Rats," American Institute of Nutrition, 1992, pp. 2440–2446.

Nippon Nōgeikagaku Kaishi, vol. 6, No. 3, Mar. 1992, pp. 218 (3Lp13).

Nagata, et al., "Stereochemical Structures of Antioxidative Bisepoxylignans, Sesaminol and its Isomers, Transformed from Sesamolin," *Agric. Biol. Chem.*, 51(5), 1285–1289, 1987.

Osawa, et al., "Sesamolinol, a Novel Antioxidant Isolated from Sesame Seeds," *Agric. Biol. Chem*, 49(11), 3351–3352, 1985.

The Merck Index, 11th Edition, 1989, p. 1343.

*Primary Examiner*—Kimberly Jordan
*Attorney, Agent, or Firm*—Burns, Doane, Swecker & Mathis, L.L.P.

[57] ABSTRACT

A food, drink, pharmaceutical, cosmetic composition or food additive comprising a dioxabicyclo[3.3.0]octane derivative represented by the following general formula (I):

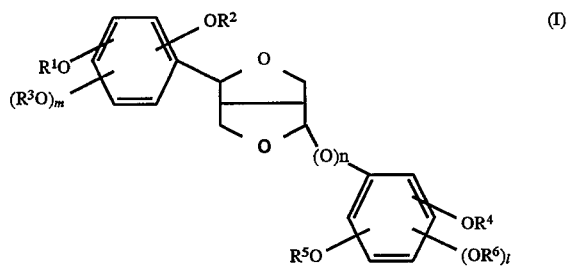

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; and antioxidant.

28 Claims, No Drawings

COMPOSITION CONTAINING DIOXABICYCLO [3.3.0] OCTANE DERIVATIVE

This application is a continuation of application Ser. No. 07/897,756, filed Jun. 12, 1992 now abandoned.

BACKGROUND OF THE INVENTION

1. Field of the Invention

The present invention relates to a food or pharmaceutical composition containing a dioxabicyclo[3.3.1]octane derivative and an antioxidant.

2. Description of the Related Art

U.S. Pat. No. 4,427,694 discloses that sesamin is effective for alleviating the symptoms of alcohol intoxication and/or alcohol or tobacco withdrawal, and Japanese Unexamined Patent Publication No. 2-138120 discloses that sesaminol and episesaminol are effective for therapeutic or prophylactic treatment of allergic diseases such as bronchial asthma.

Nevertheless, compounds which are safe and enhance the activities of dioxabicyclo[3.3.0]octane derivatives are not known, and therefore, there is a desire for a development of novel compositions providing enhanced actions of dioxabicyclo[3.3.0]octane derivatives.

Note, the present inventors have proposed various uses of dioxabicyclo[3.3.0]octane derivatives, including an inhibition of $\Delta^5$-desaturase (Japanese Unexamined Patent Publication No. 3-27319), an improvement of liver functions (Japanese Patent Application No. 2-002345), a lowering of cholesterol levels (Japanese Patent Application No. 2-002637), an inhibition of oncogenesis (Japanese Patent Application No. 2-002818), and a prevention of sickness due to alcohol (Japanese Patent Application No. 3-104016).

It is known that sesaminol, and 3 possible stereoisomers thereof, i.e., 2-episesaminol, 6-episesaminol and disesaminol are antioxidant lignan-type compounds (Agr. Biol. Chem. 51(5), 1285–1289, 1987). Sesaminol also is known as a natural antioxidant substance (Agr. Biol. Chem 49(11) 3351–3352 (1985))

U.S. Pat. No. 4,836,987 discloses compounds having lignan backbone and oxygen-containing sidechain on oxygen-containing ring, such as l-sesamin, sesamolin etc. exhibit acceleration of blood clotting action and hemostatic action.

Japanese Unexamined Patent Publication No. 60-224629 discloses an agent for inhibiting in-vivo formation of peroxidated lipid comprising sesame extract having antioxidant activity.

As a use of sesamin, insecticide synergest in known. Moreover, as a use of sesamolin, synergestics of pyrethrum insecticides are known (The MERCK INDEX 11th Edition 1989, 1343).

SUMMARY OF THE INVENTION

Accordingly, the present invention provides pharmaceutical compositions, food and drink, as well as food additives, comprising dioxabicyclo[3.3.0]octane derivatives and a compound which enhances the actions of the dioxabicyclo[3.3.0]octane derivatives.

More particularly, the present invention provides a pharmaceutical composition comprising a dioxabicyclo[3.3.0] octane derivative represented by the formula (I):

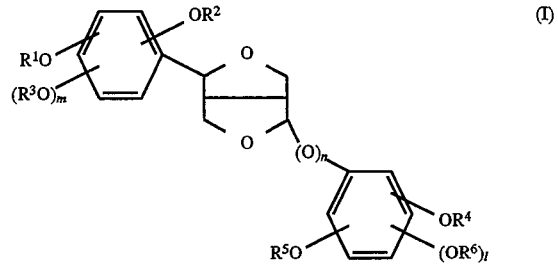

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1, and an antioxidant.

The present invention further provides a food additive comprising a dioxabicyclo[3.3.0]octane derivative represented by the following general formula (I):

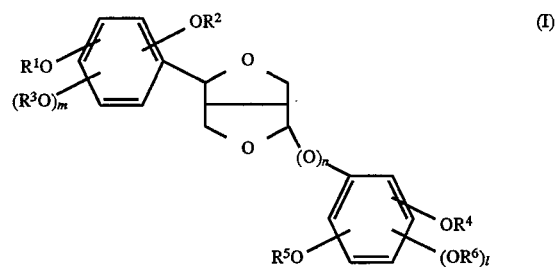

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1, and an antioxidant.

The present invention further provides a food or drink comprising a dioxabicyclo[3.3.0]octane derivative represented by the following general formula (I):

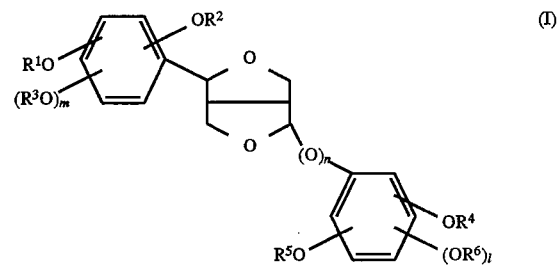

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1, and an antioxidant.

DESCRIPTION OF THE PREFERRED EMBODIMENTS

As the dioxabicyclo[3.3.0]octane derivative, in the present invention, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane can be used. These derivatives can be used alone or in the form of a mixture of two or more thereof.

The compound used in the present invention, and an extract composed mainly of the compound of the present invention, can be obtained according to the following procedures. First, an extract composed mainly of the compound of the present invention can be obtained from sesame oil, by a method comprising extracting sesame oil with an organic solvent substantially immiscible with sesame oil and capable of extracting and dissolving the compound of the present invention, and concentrating the extract. As the organic solvent, there can be mentioned, for example, acetone, methylethyl ketone, diethyl ketone, methanol and ethanol. For example, an extract composed mainly of the compound of the present invention can be obtained by mixing sesame oil homogeneously with an organic solvent as mentioned above, allowing the mixture to stand at a low temperature, carrying out a phase separation according to a customary process, and removing the solvent from the solvent fraction by evaporation.

More specifically, sesame oil is dissolved in 2 to 10 volumes, preferably 6 to 8 volumes of acetone, and the solution is allowed to stand at −80° C. overnight. As a result, the oil component is precipitated and the organic solvent is removed from the obtained filtrate by distillation, whereby an extract composed mainly of the compound of the present invention is obtained. Alternatively, sesame oil is mixed with hot methanol or hot ethanol, the mixture is allowed to stand at room temperature, and the solvent is removed from the solvent fraction to obtain an extract composed mainly of the compound of the present invention. More specifically, sesame oil is mixed with hot methanol (higher than 50° C.) or hot ethanol (higher than 50° C.) in a volume of 2 to 10 times, preferably 5 to 7 times the volume of the sesame oil, to effect a violent extraction. The phase separation is effected by a phase separation when standing at room temperature or a centrifugal separation according to customary procedures, and the solvent is removed from the solvent fraction by distillation to obtain an extract composed mainly of the compound of the present invention. Furthermore, the supercritical gas extraction can be utilized.

The compound of the present invention can be obtained from an extract as mentioned above by treating the extract by a customary method such as column chromatography, high performance liquid chromatography, recrystallization, distillation, or liquid-liquid countercurrent distribution chromatography. More specifically, by using a reversed phase column ($5C_{18}$) and methanol/water (60/40) as the eluent, the extract is subjected to high performance liquid chromatography, the solvent is removed by distillation, and the obtained crystal is recrystallized from ethanol to obtain the compound used in the present invention, such as sesamin, episesamin, sesaminol or episesaminol. The sesame oil used in the present invention can be either a purified product or a crude product. Furthermore, sesame seeds or sesame lees (defatted sesame seeds having a residual oil content of 8 to 10%) can be used. In this case, sesame seeds or sesame lees are pulverized if necessary, and then subjected to the extraction according to customary procedures using any solvent, for example, a solvent as mentioned above with respect to the extraction from sesame oil. The extraction residue is separated, and the solvent is removed from the extract by evaporation or the like to obtain an extraction product.

The compound used in the present invention, for example, sesamin, sesaminol, episesamin, episesaminol, sesamolin, 2-(3,4-methylenedioxyphenyl)-6 -(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane, can be obtained from a sesame seed extract, a sesame lee extract or a crude sesame oil extract according to the same procedures as described above. Moreover, the compound used in the present invention can be obtained from a by-product formed in the sesame oil-preparing process.

Note, sesamin obtained from *Piper longum* L exhibits the same effects as those provided by sesame seeds, sesame lee and sesame oil. Moreover, optically active isomers of the above-compounds also may be used in the present invention.

The process for the purification of the compound used in the present invention and the process for obtaining the extract are not limited to those mentioned above, and the compound used in the present invention and the extract composed mainly of the compound of the present invention are not limited to those obtained from sesame oil, sesame lees and sesame seeds, but as is apparent to persons with ordinary skill in the art, all natural substances containing the compound used in the present invention can be used. For example, there can be mentioned *Acanthopanax ghacilistylus*, Asari Herba Cum Redice, *Ginkgo-biloba* and *Piper lonqum* L.

The following processes can be adopted for the synthesis of the compound of the present invention.

For example, sesamin and episesamin can be synthesized according to the process of Beroza et al. [J. Am. Chem. Soc., 78, 1242 (1956)]. Pinoresinol [in the general formula (I), $R^1$ and $R^4$ represent H, $R^2$ and $R^5$ represent $CH_3$, and n, m and l are zero] can be synthesized according to the process of Freundenberg et al. [Chem. Ber. 86, 1157 (1953)]. Furthermore, syringaresinol [in the general formula (I), $R^1$ and $R^4$ represent H, $R^2$, $R^3$, $R^5$ and $R^6$ represents $CH_3$, n is zero, and each of m and l is 1] can be synthesized according to the process of Freundenberg et al [Chem. Ber., 88, 16 (1955)].

The compound used in the present invention also can be used in the form of a glycoside. Furthermore, compounds used in the present invention can be used alone or in combination.

As antioxidants of the present invention, there are included natural antioxidants such as tocopherols, flavone derivatives, phyllodulcins, kojic acid, gallic acid derivatives, catechins, fukinolic acid, gossypol, pyrazine derivatives, sesamol, guaiacol, guaiac resin, p-cumaric acid, nordihydroguaiaretic acid, sterols, terpenes, purine or pyrimidine bases, carotenoides and the like, as well as synthetic antioxidants such as butylhydroxyanisol (BHA), butylhydroxytoluene (BHT), mono-tert.-butyl hydroquinone (TBHQ), 4-hydroxymethyl-2,6-di-tert.-butylphenol (HMBP) and the like.

The tocopherols include α-tocopherol, β-tocopherol, γ-tocopherol, δ-tocopherol, ε-tocopherol, ξ-tocopherol, η-tocopherol, and tocopherol esters such as tocopherol acetates, and the carotenoids includes β-carotene, canxanthine, astaxanthine and the like.

As actions of dioxabicyclo[3.3.0]octane derivatives, there are known Δ5-desaturase inhibition, cholesterol uptake inhibition, cholesterol synthesis inhibition, cholesterol metabolism control, prevention or treatment of fatty liver, liver disorders caused by alcohol, treatment of liver disorders caused by chemicals, acceleration of alcohol metabolism, decrease of serum cholesterol or neutral fat, depression of parasympathetic nervous functions when eating or drinking, depression of an increase of temperature of face surface when drinking alcohol and acceleration of returning to normal temperature, and inhibition of breast cancer.

As actions of sesamin, there are known acceleration of blood clotting and hemostatic action, enhancement of insecticidal activity, psychotropically effective action and the like. Moreover, it is known that sesamolin exhibits acceleration of blood clotting and hemostatic action.

It is know that sesaminol and stereoisomers thereof, sesamobinol (2-(3,4-methylenedioxyphenyl)-6-(3-methoxy-4-hydroxyphenoxy)-3,7-dioxabicyelo[3.3.0]octone), 2-(3,4-methylenedioxyphenyl)-6-(3-methoxy-4-hydroxyphenyl)-3,4-dioxabicyclo[3.3.0]octane, pinoresinol (2,6-bis-(3-methoxy-4-hydroxyphenyl)-3,7-dioxabicyclo[3.3.0]octane have antioxidant activity.

As described above, although dioxabicyclo[3.3.0]octane derivatives have various actions, the trend of actions is as follows: control of in-vivo fatty acid metabolism, increase of dihomo-γ-linolenic acid and eicosanoid thereof, repression of inflammation and thrombus, lowering of blood pressure, improvement of liver function, inhibition of oncogenesis of colon cancer and breast cancer, prevention of sick from drink, alleviation of alcoholism, acceleration of blood clotting, prevention and treatment of cardiovascular diseases caused by high blood cholesterol, and prevention of accumulation of cholesterol in various parts of the circular system; and in case of those having antioxidant action, prevention of oxidation of oil or fat per se foods containing oil or fat and cosmetics, inhibition of active oxygen radical formed by peroxidation of cytoplasmic lipid and cellular components or by metabolism to prevent cell injury. According to the present invention, the above-mentioned actions are enhanced by combination with antioxidant such as tocopherol, and a smaller amount of the dioxabicyclo[3.3.0]octane derivative provides significant activities.

According to the present invention, although a ratio of dioxabicyclo[3.3.0]octane and antioxidant is not critical, particularly for an enhancing of the dioxabicyclo[3.3.0]octane derivatives actions, especially the cholesterol-lowering action, the ratio of dioxabicyclo[3.3.0]octane/antioxidant is preferably between 0.001 and 1000, more preferably 0.01 to 20, more preferably 0.1 to 20, most preferably 0.2 to 10.

The present compositions are provided as pharmaceutical compositions, cosmetic, food or drinks, or food additives. The pharmaceutical compositions may be administered exterally, or parenterally, for example, intramuscularly, subcutaneously, or intravenously.

The dosage varies depending on the purpose of the administration and the conditions of subjects receiving the composition, but to lower the cholesterol level, a dose for an oral administration is generally 1 to 100 mg/day, and a dose for a parenteral administration is 0.1 to 20 mg/day, for an adult human. To prepare an injectable composition, a medical solubilizing agent such as nonionic surfactant can be used.

More particularly, the present pharmaceutical composition can be prepared, for example, by dissolving a compound of the present invention in 80 volume of POE(60)-hardened castor oil, or nonionic surfactant such as POE sorbitan mono oleate with heating, and diluting the resulting mixture with a physiological saline. Optionally, an isotonic agent, stabilizer, a preservative, an analgesic and the like may be added. Moreover, if necessary, emulsions capsules, powders, granules, tablets and the like may be prepared.

The present invention further provides food additives comprising dioxabicyclo[3.3.0]octane derivatives and antioxidant. The addition of the additive is useful because most foods do not contain the same or contain only a very little amount thereof.

The present invention still further relates to food or drink to which dioxabicyclo[3.3.0]octane derivatives and/or an antioxidant is added. Since most food and drink does not contain, or contains in only a very small amount, both of the above ingredients, then the present food or drink can be produced by adding both ingredients to such a food or drink. Nevertheless, some food already contains a sufficient amount of dioxabicyclo[3.3.0]octane derivative, such as sesamin, and thus it is sufficient to add only an antioxidant for the production of the present food and drink. Since dioxabicyclo[3.3.0]octane derivatives, which are active ingredients of the present compositions, are compounds or analogues thereof found in conventional food, they are advantageous from a safety point of view. Moreover, if antioxidants, able to enhance the actions of dioxabicyclo[3.3.0]octane derivatives are selected from those conventionally used as antioxidants, they are harmless and have no effect on the taste of the food or drink.

The food of the present invention, and food to which the present food additives are added is not limited, but considering the cholesterol level-lowering action, food containing fat or oil may be considered.

For example, there may be mentioned natural food containing fat or oil, such as meat, fish, nuts and the like; food to which fat or oil is added during the cooking thereof, such as Chinese food, Chinese noodle, soup and the like; food cooked using fat or oil as a heating medium, such as Japanese Tempura, fried food, Chinese fried rice, doughnuts, sugar-coated fries and the like; fatty food such as butter, margarine, mayonnaise, salad dressing, chocolate, instant noodles, caramel, biscuits, ice cream and the like; and food sprayed or coated with a fat or oil at finish, etc. Since the addition of the present composition to oil or fat is easy, the present composition is preferably added to fat or oil. Nevertheless, the food to which the present composition is added is not limited, and the present composition may be added to any food to thereby enhance the dioxabicyclo[3.3.0]octane derivative action of such food.

For food containing the present composition, although the amounts of dioxabicyclo[3.3.0]octane derivative and antioxidant are not critical, the dioxabicyclo[3.3.0]octane derivatives are preferably used alone or as a mixture in an amount of at least 0.0001% by weight, more preferably at least 0,001% by weight in total, on the basis of the weight of the food; and antioxidants are preferably added alone or as a mixture in an amount of at least 0.00001% by weight, more preferably at least 0.0001% by weight in total, on the basis of the weight of the food. Where an extract containing dioxabicyclo[3.3.0]octane derivatives is used, the extract is preferably used in an amount of at least 0.0004% by weight, more preferably at least 0.004% by weight, on the basis of the weight of the food.

Since dioxabicyclo[3.3.0]octane derivatives, an active ingredient of the present composition, are compounds present in conventional food or analogues thereof, then the food containing dioxabicyclo[3.3.0]octane derivatives potentially should have the activities of dioxabicyclo[3.3.0]octane derivatives. In actuality, however, the food does not sufficiently exhibit the actions of dioxabicyclo[3.3.0]octane derivatives, because the content thereof is too low.

Accordingly, in one embodiment of the present invention, an antioxidant of the present invention is added to a food containing dioxabicyclo[3.3.0]octane derivative in an amount of 0.001 to 1000 parts by weight, preferably 0.01 to 20 parts by weight, more preferably 0.1 to 20 parts by weight, most preferably 0.2 to 10 parts by weight, relative to one part by weight of dioxabicyclo[3.3.0]octane derivative contained therein, to enhance the actions of dioxabicyclo[3.3.0]octane derivatives, especially the cholesterol level lowering action.

Where food or drink containing dioxabicyclo[3.3.0]octane derivative also contains an antioxidant, which enhances the actions of the dioxabicyclo[3.3.0]octane derivative, the same or a different antioxidant can be further added to the food or drink in a total amount of up to 1000 parts by weight, preferably up to 100 parts by weight, more preferably up to 20 parts by weight, most preferably up to 10 parts by weight, relative to one part by weight of the dioxabicyclo[3.3.0]octane derivative, to obtain food or drink having further enhanced actions, such as a cholesterol level lowering action, of the dioxabicyclo[3.3.0]octane derivative. Where tocopherol is used as an antioxidant, for example, where food or drink containing the dioxabicyclo[3.3.0] octane derivative does not contain an antioxidant, the tocopherol may be added to the food or drink in an amount of 0.01 to 100 parts by weight, preferably 0.1 to 20 parts by weight, most preferably 0.2 to 10 parts by weight, relative to one part by weight dioxabicyclo[3.3.0]octane derivative, to enhance the actions, such as the cholesterol level lowering action, of the dioxabicyclo[3.3.0]octane derivative.

As food containing dioxabicyclo[3.3.0]octane derivatives, there can be mentioned sesame, washed sesame, peeled sesame, roasted sesame, roasted and peeled sesame, sesame paste, milled sesame, kneaded sesame, sesame curd, sesame salad oil, roasted sesame oil, sesame powder and the like. Note, food to which an antioxidant is added is not limited to sesame-based food, and the present antioxidants may be added to any food containing dioxabicyclo[3.3.0] octane derivatives to thereby enhance the actions of the dioxabicyclo[3.3.0]octane derivative.

According to the present invention a combination of a dioxabicyclo[3.3.1]octane derivative and antioxidant provide a synergistic action, such as synergistic lowering of cholesterol level.

EXAMPLES

Next, the present invention is further described in the following Examples.

Example 1.

First, 36 male SD rats, 5 weeks old, were prefed with a standard feed (solid CE-2, Nippon Clea) for one week, and then were divided into 6 groups each consisting of 6 animals. The animals were fed for two weeks with a cholesterol-enriched feed comprising 20% casein, 10% powdered beef tallow, 56.75% granule sugar, 4% cellulose, 1% cholesterol, 0.25% cholic acid, 1% vitamin mixture (AIN-TM) and 7% mineral mixture (TIN-TM), or experimental feed supplemented with tocopherol acetate and/or sesamin, in different amounts. The experimental groups were set as follows:

1. Cholesterol feed
2. Cholesterol feed+1.0% tocopherol acetate
3. Cholesterol feed+0.05% sesamin
4. Cholesterol feed+0.05% sesamin+1.0% tocopherol acetate
5. Cholesterol feed+0.2% sesamin
6. Cholesterol feed+0.2% sesamin+1.0% tocopherol acetate The above-mentioned tocopherol was DL-α-tocopherol acetate (Nacalai Tesque), and the above-mentioned "sesamin" means a mixture of sesamin and episesamin (sesamin 55.2%, episesamin 44.4%, purity 99.6%) prepared according to a procedure described in Japanese Unexamined Patent Publication No. 3-27319.

After being fed for 2 weeks, the animals were starved, and blood samples were taken. The total cholesterol, HDL-cholesterol, triglycenide phospholipid, GOT and GPT levels in the sera were measured using a biochemical automatic analyzer (Hikachi Model 7050). The LDL-cholesterol value was obtained by calculation. The results are shown in Table 1.

TABLE 1

|  | Cholesterol feed | Cholesterol feed + 1.0% V.E. | Cholesterol feed + 0.05% SES. | Cholesterol feed + 0.05% SES. + V.E. | Cholesterol feed + 0.2% SES. | Cholesterol feed + 0.2% SES. + V.E. |
| --- | --- | --- | --- | --- | --- | --- |
| TC (mg/dl) | 490 ± 229 | 460 ± 172 | 437 ± 187 | 244 ± 57* | 371 ± 68 | ***149 ± 21* |
| (%) | 100 | 94 | 89 | 50 | 76 | 30 |
| LDL-C (mg/dl) | 456 ± 221 | 421 ± 174 | 405 ± 181 | *213 ± 55* | 346 ± 71 | ***109 ± 19* |
| (%) | 100 | 92 | 89 | 47 | 76 | 24 |
| HDL-C (mg/dl) | 17.8 ± 8.4 | 9.9 ± 0.9 | 10.5 ± 3.0 | 13.1 ± 2.4 | 10.3 ± 3.0 | ***24.2 ± 5.7 |
| (%) | 100 | 56 | 59 | 74 | 58 | 136 |
| LDL-C/HDL-C | 26 | 43 | 39 | 16 | 34 | 4.5 |
| PL (mg/dl) | 176 ± 52 | 186 ± 39 | 168 ± 43 | 126 ± 23 | 150 ± 18 | **122 ± 25* |
| TG (mg/dl) | 79 ± 32 | 135 ± 49* | 91 ± 28 | 90 ± 44 | 71 ± 23 | 71 ± 24 |
| GOT (IU/l) | 129 ± 11 | 172 ± 66 | 157 ± 34 | 124 ± 8 | 120 ± 16 | 119 ± 18 |
| GPT (IU/l) | 27 ± 3 | 65 ± 48 | 37 ± 10 | 27 ± 3 | 24 ± 2 | *34 ± 8 |

TC: Total cholesterol
LDL-C: LDL-cholesterol
HDL-C: HDL-cholesterol
LDL/HDL-C: sclerosis factor
TG: Triglyceride
PL: phospholipid
SES: sesamin
V.E.: tocopherol acetate
LDL-C = TC-(TG/5 + HDL-C)
Significant defference to cholesterol feed
*$P < 0.05$
**$P < 0.01$
***$P < 0.001$
Significant defference to cholesterol feed and 0.2% sesamin
★$< 0.05$
★★$< 0.01$
★★★$< 0.001$ An increase of total serum cholesterol value provided by the cholesterol feed was inhibited in a dose-dependent manner, and the inhibition was remarkably enhanced by the addition of tocopherol. In the animal group to which tocopherol alone was provided, the total serum cholesterol level was not significantly changed, revealing that tocopherol enhances the action of sesamin in lowering the cholesterol level.

Example 2.

First, 27 SD rats, 5 seeks old, were prefed with a standard feed (solid CE-2, Nippon Clea) for one week, and then were divided into 4 groups consisting of 6 or 9 animals. According to a similar procedure as described in Example 1, the animals were fed with a cholesterol feed, or with a cholesterol feed supplemented with tocopherol acetate and/or sesamin, for 2 weeks. The experimental groups were as follows:

1. Cholesterol feed
2. Cholesterol feed+0.2% sesamin
3. Cholesterol feed+0.2% sesamin+0.2% tocopherol acetate
4. Cholesterol feed+0.2% sesamin+1.0% tocopherol acetate The above-mentioned tocopherol and sesamin were the same as described in Example 1. After being fed for 2 weeks, the animals were starved for 17 hours, and then blood samples were taken. The total cholesterol, HDL-cholesterol, triglyceride, phospholipid, GOT, and GPT levels in the serum were measured using an automatic biochemical analyzer. The LDL-cholesterol value was calculated. The results are shown in Table 2.

Example 3.

Sesaminol (Compound A) prepared from purified sesame oil according to Japanese Unexamined Patent Publication No. 1-243992, 2-(3,4-methylenedioxyphenyl)-6-(3-methoxy-4-hydroxyphenyl)-3,7-dioxabicyclo[3.3.0]octane (Compound C) prepared by extracting sesame seeds with acetone, 2,6-bis-(3-methoxy-4-hydroxyphenyl)-3,7-dioxabicyclo[3.3.0]octane (Compound D), or 2-(3,4-methylenedioxyphenyl)-6-(3-methoxy-4-hydroxyphenoxy)-3,7-dioxabicyclo[3.3.0]octane (Compound E) were used in the following experiments.

First, 42 SD rats, 5 weeks old, were prefed with a standard feed (solid E-2, Nippon Clea), and were then divided into 7 groups each consisting of 6 animals. Next, the animals were fed with the cholesterol feed as described in Example 1, or an experimental feed supplemented with tocopherol acetate and/or Compound A, B, C, D or E, for 2 weeks. The experimental groups were as follows:

1. Cholesterol feed
2. Cholesterol feed+0.2% sesamin
3. Cholesterol feed+0.2% Compound A+1.0% tocopherol acetate
4. Cholesterol feed+0.2% Compound B+1.0% tocopherol acetate
5. Cholesterol feed+0.2% Compound C+1.0% tocopherol acetate
6. Cholesterol feed+0.2% Compound D+1.0% tocopherol acetate
7. Cholesterol feed+0.2% Compound E+1.0% tocopherol acetate The above-mentioned tocopherol acetate was the same as used in Example 1. After being fed two weeks, the animals

TABLE 2

|  | Cholesterol feed<br>N = 9 | Cholesterol feed +<br>0.2% SES.<br>N = 6 | Cholesterol feed +<br>0.2% SES. +<br>0.2% V.E.<br>N = 6 | Cholesterol feed +<br>0.2% SES. +<br>1.0% V.E.<br>N = 6 |
| --- | --- | --- | --- | --- |
| Total cholesterol | 492 ± 66 | 374 ± 157 | 243 ± 11*** | 184 ± 32*** |
| (TC) (mg/dl) | 100 | 76 | 49 | 37 |
| (%) |  |  |  |  |
| LDL-cholesterol[1] | 471 ± 65 | 349 ± 156*** | 217 ± 12*** | 154 ± 29*** |
| (LDL-C) (mg/dl) | 100 | 74 | 46 | 33 |
| (%) |  |  |  |  |
| HDL-cholesterol | 7.3 ± 1.7 | 10.0 ± 2.6* | 12.8 ± 4.3* | 17.7 ± 2.8*** |
| (HDL-C) (mg/ld) | 100 | 137 | 175 | 242 |
| (%) | 64.5 | 34.9 | 17.0 | 8.7 |
| LDL-C/HDL-C[2] |  |  |  |  |
| Phospholipid | 185 ± 32 | 161 ± 41 | 137 ± 18** | 121 ± 12*** |
| (PL) (mg/dl) |  |  |  |  |
| Triglyceride | 67.0 ± 25.2 | 71.6 ± 27.4 | 64.4 ± 21.5 | 63.4 ± 34.0 |
| (TG) (mg/dl) |  |  |  |  |
| GOT (IU/l) | 152 ± 28 | 147 ± 29 | 155 ± 17 | 142 ± 18 |
| GPT (IU/l) | 39 ± 8 | 34 ± 6 | 41 ± 9 | 34 ± 5 |

[1]LDL-C = TC-(TG/5 + HDL-C)
[2]LDL-C/HDL-C: sclerosis index
SES: sesamin
V.E.: tocopherol acetate
Significant difference to cholesterol feed
*P < 0.05
**P < 0.01
***P < 0.001

It was found that tocopherol enhanced the actions of sesamin in a dose-dependent manner, thus revealing the usefulness of the present composition.

were starved for 17 hours, and then blood samples were taken. The total cholesterol level was measured using an automatic biochemical analyzer, and as a result, it was confirmed that the up-take of tocopherol acetate significantly enhances the action of each compound in lowering the cholesterol level. Although the total cholesterol value in the serum of the first group was increased to 419±153 mg/dl by the cholesterol feed, the administration of sesamin to the second group reduced the cholesterol value to 361±128 mg/dl. For the groups 3, 4, 5, 6 and 7, wherein Compounds A, B, C, D and E with tocophenol acetate were additionally administered, the total cholesterol values were 198±33, 204±42, 186±37, 211±61 and 218±57 mg/dl respectively, revealing that the Compound A, B, C, D or E used in combination with tocophenol further inhibited the increase of the total cholesterol level value.

Example 4.

First, 100 g of butter fat prepared by eliminating butter milk during the production of butter by the stirring operation (churning) was mixed with 1.2 g of a mixture of sesamin and episesamin used in Example 1 and 1.2 g of tocopherol acetate, and the kneading operation (working) was carried out to obtain a homoqeneous cholesterol level lowering butter containing the present composition.

Formulation Example 1.

First, 0.25 g of sesamin and 0.25 g of tocopherol acetate were mixed with 20.5 g of silicic anhydride, and 79 g of corn starch was added thereto, followed by a further mixing. Then to the mixture was added 100 ml of 10% hydroxypropylcellulose ethanol solution, the mixture was kneaded and extruded, and the resulting granules were dried.

Formulation Example 2.

First, 3.5 g of sesamin and 0.5 g of tocopherol acetate were mixed with 20 g of silicic anhydride, and to the mixture were then added 10 g of microcrystalline cellulose, 3.0 g of magnesium stearate, and 60 g of lactose. The mixture was pressed to form tablet having a diameter of 7 mm and a weight of 100 mg by using a single-shot tableting machine.

Formulation Example 3.

First, 1.25 g of sesamin and 1.25 g tocopherol acetate were dissolved in 200 g of a nonionic surface active agent TO-1014 (Nikko Chemicals) while heating at 122° C., and 4.7975 l of sterilized physiological saline was added thereto. The mixture was then thoroughly stirred, aseptically filled in vials, which were then closed, to obtain an injectable formulation.

We claim:

1. A pharmaceutical composition comprising a dioxabicyclooctane derivative represented by the following general formula (I):

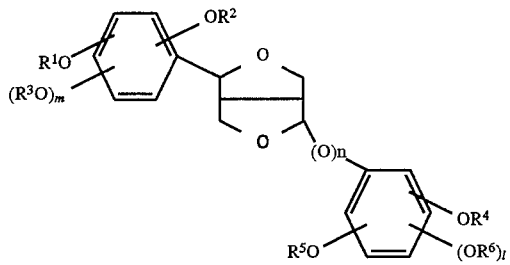

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; and an antioxidant, wherein the ratio of dioxabicyclooctane derivative to antioxidant is from about 0.05 to 20.

2. A pharmaceutical composition according to claim 1, wherein the dioxabicyclooctane derivative is sesamin, sesaminol, episesamin, episesaminol, sesamolin, 2-(3,4-methylenedioxyphenyl)-6-(3-methoxy-4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxyphenoxy)-3,7-dioxabicyclooctane.

3. A pharmaceutical composition according to claim 1, wherein the antioxidant is tocopherol.

4. A pharmaceutical composition according to claim 1, wherein the action of dioxabicyclooctane derivative is lowering cholesterol value.

5. A food additive comprising a dioxabicyclooctane derivative represented by the following general formula (I):

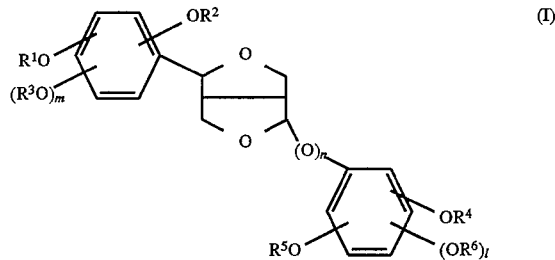

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; and an antioxidant, wherein the ratio of dioxabicyclooctane derivative to antioxidant is from about 0.05 to 20.

6. A food additive according to claim 5, wherein the dioxabicyclooctane derivative is sesamin, sesaminol, episesamin, episesaminol, sesamolin, 2-(3,4-methylenedioxyphenyl)-6-(3-methoxy-4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxyphenoxy)-3,7-dioxabicyclooctane.

7. A food additives according to claim 5, wherein the antioxidant is tocopherol.

8. A food additive according to claim 5, wherein the action of dioxabicyclooctane derivative is lowering cholesterol value.

9. A food or drink to which a dioxabicyclooctane derivative represented by the following general formula (I):

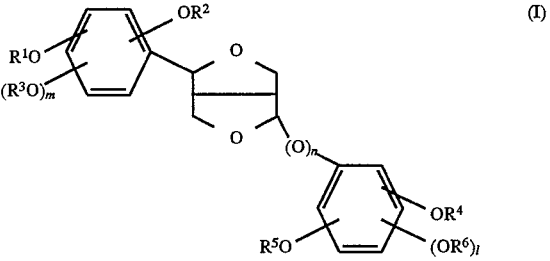

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; and an antioxidant have been added, wherein the ratio of dioxabicyclooctane derivative to antioxidant is from about 0.05 to 20.

10. A food or drink according to claim 9, wherein the dioxabicyclooctane derivative is sesamin, sesaminol, episesamin, episesaminol, sesamolin, 2-(3,4-methylenedioxyphenyl)-6-(3-methoxy-4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxyphenoxy)-3,7-dioxabicyclooctane.

11. A food or drink according to claim 9, wherein the antioxidant is tocopherol.

12. A food or drink exhibiting enhanced actions of dioxabicyclooctane derivative prepared by adding an antioxidant to a food or drink containing dioxabicyclo-octane derivative, wherein the ratio of dioxabicyclo-octane derivative to antioxidant is from about 0.05 to 20, wherein the dioxabicyclooctane derivative is represented by the formula (I):

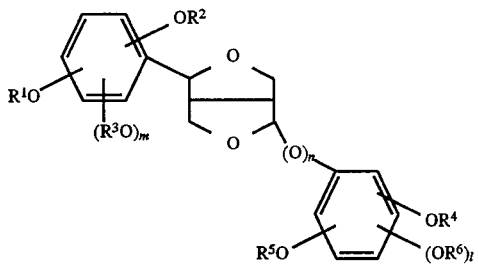

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

13. A food or drink according to claim 12, wherein the antioxidant is tocopherol.

14. A food or drink according to claim 12, wherein the dioxabicyclooctane derivative is sesamin, sesaminol, episesamin, episesaminol, sesamolin, 2-(3,4-methylenedioxyphenyl)-6-(3-methoxy-4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxy-phenoxy)-3,7-dioxabicyclooctane.

15. A method for lowering cholesterol value in a mammal comprising adding to a food or drink a dioxabicyclooctane derivative represented by the following general formula (I):

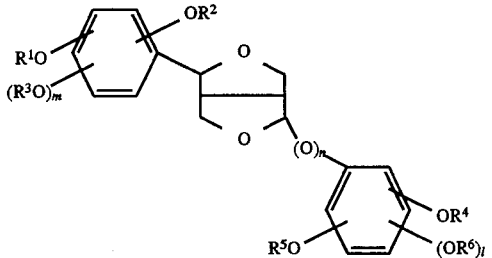

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; and an antioxidant, wherein the ratio of dioxabicyclooctane derivative to antioxidant is from about 0.05 to 20, and administering the food or drink to a mammal in an amount effective for lowering the cholesterol value of said mammal.

16. A method according to claim 15, wherein an effective amount is 1 to 100 mg/day of dioxabicyclooctane derivative and antioxidant orally administered to an adult human.

17. A method according to claim 15, wherein an effective amount is 0.1 to 20 mg/day of dioxabicyclooctane derivative and antioxidant parenterally administered to an adult human.

18. A method according to claim 15, wherein the dioxabicyclooctane derivative is sesamin, sesaminol, episesamin, episesaminol, sesamolin, 2-(3,4-methylenedioxyphenyl)-6-(3-methoxy -4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxy-phenoxy)-3,7-dioxabicyclooctane.

19. A method according to claim 15, wherein the antioxidant is tocopherol.

20. A pharmaceutical composition comprising a sesamin and/or an episesamin and tocopherol so that the ratio of the sesamin and/or episesamin to the tocopherol is from about 0.05 to 20.

21. A method for enhancing in vivo an action of a dioxabicyclooctane derivative represented by the following general formula (I):

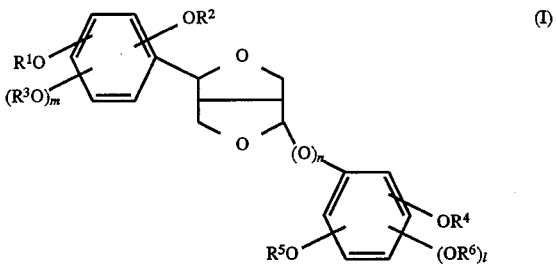

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1; comprising blending the dioxabicyclooctane derivative With an antioxidant, wherein the ratio of dioxabicyclooctane derivative to antioxidant is from about 0.05 to 20; and administering the mixture to a mammal in an amount effective for enhancing in vivo the action of the dioxabicyclooctane derivative in said mammal.

22. A method according to claim 21, wherein the dioxabicyclooctane derivative is sesamin, sesaminol, episesamin, episesaminol, sesamolin, 2-(3,4-methylenedioxyphenyl)-6-(3-methoxy-4-hydroxyphenyl)-3,7-dioxabicyclooctane, 2,6-bis-(3-methoxy-4-hydroxyphenyl)-3,7-dioxabicyclooctane or 2-(3,4-methylenedioxyphenyl)-6-(3-methoxy-4-hydroxyphenoxy)-3,7-dioxabicyclooctane.

23. A method according to claim 21, wherein the antioxidant is tocopherol.

24. A method according to claim 21, wherein 1 to 100 mg/day of the dioxabicyclooctane derivative and antioxidant mixture are orally administered to an adult human.

25. A method according to claim 21, wherein an effective amount is 0.1 to 20 rag/day of dioxabicyclooctane derivative and antioxidant parenterally administered to an adult human.

26. A method according to claim 21, wherein an effective amount is 1 to 100 mg/day of the dioxabicyclooctane derivative and antioxidant mixture orally administered to an adult human.

27. A method according to claim 21, wherein an effective amount is 0.1 to 20 mg/day of dioxabicyclooctane derivative and antioxidant parenterally administered to an adult human.

28. A method according to claim 21, wherein the action of dioxabicyclooctane derivative is lowering cholesterol value.

* * * * *